United States Patent [19]
Andresen et al.

[11] Patent Number: 6,114,568
[45] Date of Patent: Sep. 5, 2000

[54] PROCESS FOR ALKYLATING HINDERED SULFONAMIDES USEFUL IN THE PRODUCTION OF MATRIX METALLOPROTEINASE INHIBITORS

[75] Inventors: Brian Michael Andresen, Mystic; Phillip Dietrich Hammen, East Haddam; Joel Michael Hawkins, Old Lyme, all of Conn.

[73] Assignee: Pfizer Inc., New York, N.Y.

[21] Appl. No.: 09/289,454

[22] Filed: Apr. 9, 1999

Related U.S. Application Data

[60] Provisional application No. 60/081,310, Apr. 10, 1998.

[51] Int. Cl.$^7$ .................. C07C 303/40; C07C 311/37; C07D 311/00

[52] U.S. Cl. .................. 560/12; 560/13; 562/427; 562/430; 549/397

[58] Field of Search .................. 560/12, 13; 562/427, 562/430; 549/397

[56] References Cited

FOREIGN PATENT DOCUMENTS

96/27583  9/1996  WIPO .
98/07697  2/1998  WIPO .

*Primary Examiner*—Peter O'Sullivan
*Attorney, Agent, or Firm*—Peter C. Richardson; Paul H. Ginsburg; E. Victor Donahue

[57] ABSTRACT

The present invention relates to a process for alkylating hindered sulfonamides useful as intermediates in the preparation of matrix metalloproteinase inhibitors.

12 Claims, No Drawings

PROCESS FOR ALKYLATING HINDERED SULFONAMIDES USEFUL IN THE PRODUCTION OF MATRIX METALLOPROTEINASE INHIBITORS

The present application claims priority under 35 USC section 119(e) to United States provisional application 60/081,310 filed Apr. 10, 1998, the text of which is incorporated by reference as if fully set forth herein. The text of and claims of the United States utility application entitled "Process for Alkylating Hindered Sulfonamides" filed Apr. 9, 1999 and bearing Express Mail Label EE645346913US is also incorporated by reference as if fully set forth herein.

BACKGROUND OF THE INVENTION

The present invention relates to a process for alkylating hindered sulfonamides by Michael addition to propiolates and to novel intermediates prepared in said process. The products of the aforesaid reaction can be converted into matrix metalloproteinase inhibitors.

Inhibitors of matrix metalloproteinase (MMP) are known to be useful for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by inhibition of metalloproteinase or ADAM (including TNF-α) expression. In addition, the products which can be prepared from the compounds and processes of the present invention may be used in combination therapy with standard non-steroidal anti-inflammatory drugs (hereinafter NSAID'S), COX-2 inhibitors and analgesics for the treatment of arthritis, and in combination with cytotoxic drugs such as adriamycin, daunomycin, cis-platinum, etoposide, taxol, taxotere and alkaloids, such as vincristine, in the treatment of cancer.

The alkylsulfonamides that can be prepared by the methods of the present invention are described in the literature. PCT Publications WO 96/27583 and WO 98/07697, published Mar. 7, 1996 and Feb. 26, 1998, respectively, refer to arylsulfonyl hydroxamic acids. The above references refer to methods of preparing sulfonamides using methods other than those described in the present invention. Each of the above referenced publications is hereby incorporated by reference in its entirety.

SUMMARY OF THE INVENTION

The present invention relates to a compound of the formula

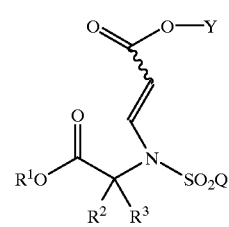

IV wherein $R^1$) is $(C_1-C_6)$alkyl or optionally substituted benzyl;

$R^2$ and $R^3$ are independently $(C_1-C_6)$alkyl or $R^2$ and $R^3$ are taken together to form a three to seven membered cycloalkyl, a pyran-4-yl ring or a bicyclo ring of the formula

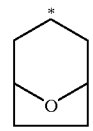

wherein the asterisk indicates the carbon atom common to $R^2$ and $R^3$;

Q is $(C_1-C_6)$alkyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_6-C_{10})$aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_{10})$aryl$(C_6-C_{10})$aryl, $(C_6-C_{10})$aryl$(C_6-C_{10})$aryl$(C_2-C_9)$heteroaryl, $(C_2-C_9)$heteroaryl$(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryloxy$(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$alkoxy$(C_1-C_6)$alkyl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl;

wherein each $(C_6-C_{10})$aryl or $(C_2-C_9)$heteroaryl moieties of said $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_6-C_{10})$aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_6-C_{10})$aryl$(C_6-C_{10})$aryl, $(C_6-C_{10})$aryl$(C_2-C_9)$heteroaryl, $(C_2-C_9)$heteroaryl$(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryloxy$(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$alkoxy$(C_1-C_6)$alkyl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro$(C_1-C_3)$alkyl, perfluoro$(C_1-C_3)$alkoxy and $(C_6-C_{10})$aryloxy;

and Y is hydrogen, $(C_1-C_6)$alkyl or a suitable protecting group.

Preferred compounds of formula IV are those wherein $R^2$ and $R^3$ are taken together to form a cyclobutyl, cyclopentyl, pyran-4-yl ring or a bicyclo ring of the formula

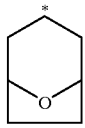

wherein the asterisk indicates the carbon atom common to $R^2$ and $R^3$;

and wherein Q is 4-(4-fluorophenoxy)phenyl.

The present invention also relates to a process for preparing a compound of the formula

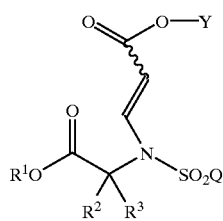

IV wherein $R^1$, $R^2$, $R^3$, Q and Y are as defined above;
comprising, reacting a compound of the formula

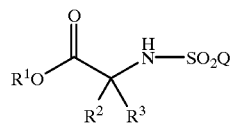

V wherein $R^1$ is optionally substituted benzyl; and $R^2$, $R^3$, and Q are as defined above;
with a compound of the formula

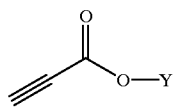

VI wherein Y is $(C_1-C_6)$alkyl;

in the presence of a base, such as tetrabutylammonium fluoride, potassium carbonate, tertiary amines and cesium carbonate, preferably tetrabutylammonium fluoride, and a polar solvent, such as tetrahydrofuran, acetonitrile, tert-butanol, t-amyl alcohols and N,N-dimethylformamide, preferably tetrahydrofuran.

The present invention also relates to a process comprising reducing said compound of the formula

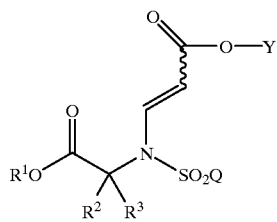

IV wherein $R^1$, $R^2$, $R^3$, Y and Q are as defined above;
with a reducing agent, such as palladium catalysts and a source of hydrogen, preferably hydrogen over palladium on carbon, in a solvent, such as alcohols or tetrahydrofuran, preferably ethanol, to form a compound of the formula

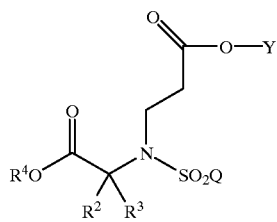

III wherein $R^4$ is hydrogen; and
$R^2$, $R^3$, Y and Q are as defined above.

The present invention also relates to a process further comprising reacting said compound of formula III, wherein $R^4$ is hydrogen, with amines such as dicyclohexylamine to form the amine salts such as dicyclohexylammonium salt of the compound of formula III.

The term "protecting group" as a substituent for Y is as described in Greene and Wuts, *Protective Groups in Organic Synthesis*, (John Wiley & Sons, Inc., Wiley Interscience Second Edition, 1991).

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl. Preferred heteroaryls include pyridyl, furyl, thienyl, isothiazolyl, pyrazinyl, pyrimidyl, pyrazolyl, isoxazolyl, thiazolyl or oxazolyl. Most preferred heteroaryls include pyridyl, furyl or thienyl.

The term "acyl", as used herein, unless otherwise indicated, includes a radical of the general formula R—(C=O)— wherein R is alkyl, alkoxy, aryl, arylalkyl or arylalkoxy and the terms "alkyl" or "aryl" are as defined above.

The term "acyloxy", as used herein, includes O-acyl groups wherein "acyl" is defined above.

The squiggly line

(i.e. " ")

in formula IV indicates that the carboxy group can exist in either a cis or trans configuration.

The compounds of formulae I–V may have chiral centers and therefore exist in different diasteriomeric or enantiomeric forms. This invention relates to all optical isomers, tautomers and stereoisomers of the compounds of formula I–V and mixtures thereof.

Preferably, compounds of the formula I' exist as the exo isomer of the formula

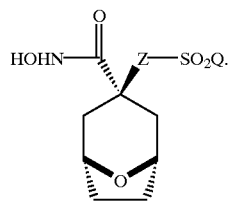

I'

Enhanced Synthesis Routes of Improved Yield

The present invention is also directed to enhanced methodology for the preparation of compounds such as structure (formula) I in Scheme I (see the Detailed Description of the Invention below),

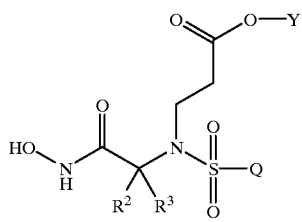

I and to novel process intermediates useful in this regard. The compounds of structure I have valuable pharmacological activities. Accordingly, there are provided preferred intermediate compounds according to structure IV as aforementioned,

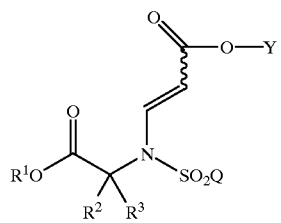

IV in which $R^1$ is $[(A_1)CH_2]_c[(A_2)CH_2]_b[(A_3)CH_2]_aC—$, where a, b, and c are each 1; and each of $A_1$, $A_2$, and $A_3$ is independently selected from the group consisting of H, $(C_1–C_5)$ alkyl, and phenyl or substituted phenyl.

In a preferred example $R^1$ is t-butyl; and thus $A_1$, $A_2$, $A_3$ are each hydrogen.

As described in greater detail below, the provision of such intermediates facilitates high yield synthesis of pharmaceutical compounds of the invention. Briefly, it has been determined that in the Michael addition reaction (see below, for its use in preliminary synthetic steps herein) wherein a compound of the formula

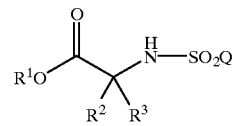

is reacted with a compound of the formula

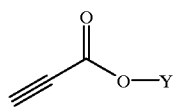

substantial and surprising advantage results if the $R^1$ group is defined according to this particular example of the invention ($R^1$ is $[(A_1)CH_2]_c[(A_2)CH_2]_b[(A_3)CH_2]_aC—$, where a, b, and c are each 1; and each of $A_1$, $A_2$, and $A_3$ is independently selected from the group consisting of H, $(C_1–C_5)$ alkyl, and phenyl or substituted phenyl), in comparison with other examples of $R^1$ as defined by the present disclosure, including for example the benzyl group.

The present invention therefore provides processes for preparing compounds such as

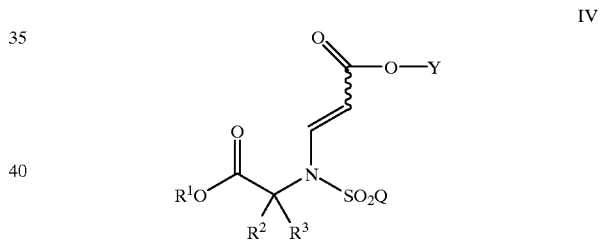

IV in which $R^1$ is $[(A_1)CH_2]_c[(A_2)CH_2]_b[(A_3)CH_2]_aC—$, where a, b, and c are each 1; and each of $A_1$, $A_2$, and $A_3$ is independently selected from the group consisting of H, $(C_1–C_5)$ alkyl, and phenyl or substituted phenyl, and processes for the further use thereof.

Such further processes include reducing said compound IV

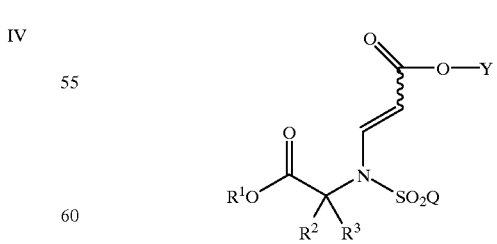

IV wherein $R^1$ is $[(A_1)CH_2]_c[(A_2)CH_2]_b[(A_3)CH_2]_aC—$, where a, b, and c are each 1; and each of $A_1$, $A_2$, and $A_3$ is independently selected from the group consisting of H, $(C_1–C_5)$ alkyl, and phenyl or substituted phenyl, and $R^2$, $R^3$, Y and Q are as defined above, with a reducing agent to form a compound of the formula

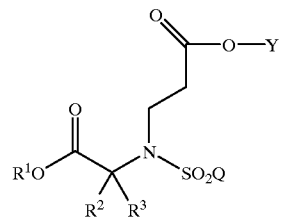

In a further aspect of the invention, said methodology further comprises hydrolyzing the above compound, wherein $R^1$, $R^2$, $R^3$, Y and Q are as defined in above, under acidic conditions to form a compound of the formula

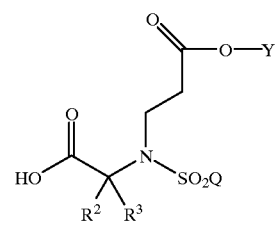

wherein $R^2$, $R^3$, Y and Q are as defined above.

In an alternate embodiment of the invention, a compound of the formula

IV

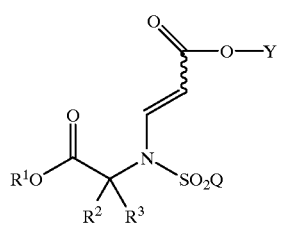

wherein $R^1$, $R^2$, $R^3$, Y and Q are as defined above, is first subject to hydrolysis under acidic conditions to form a compound of the formula (a)

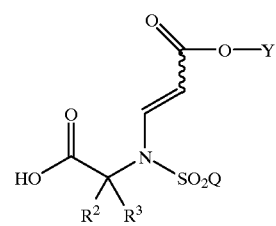

wherein $R^2$, $R^3$, Y and Q remain as defined above; and then subject to a second step in which compound (a) is treated with a reducing agent to form a compound of the formula (b)

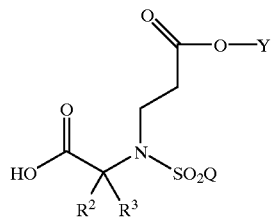

wherein $R^2$, $R^3$, Y and Q are defined as above.

DETAILED DESCRIPTION

The following reaction Schemes illustrate the preparation of the compounds of the present invention. Unless otherwise indicated n, $R^1$, $R^2$, $R^3$, Q and Z in the reaction Schemes and the discussion that follow are defined as above.

SCHEME 1

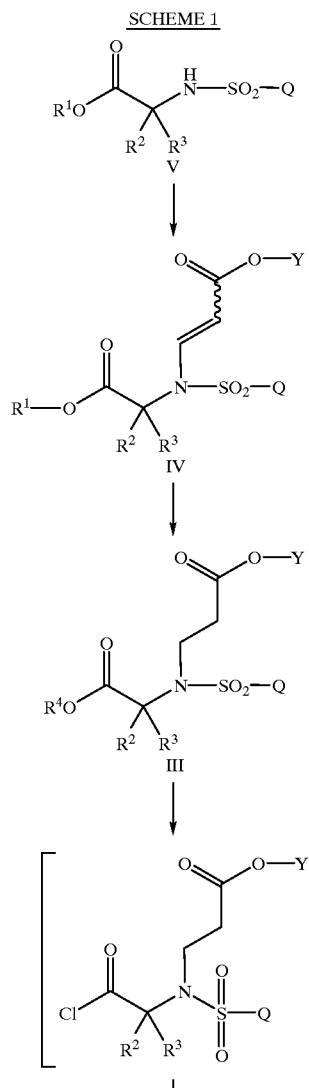

-continued

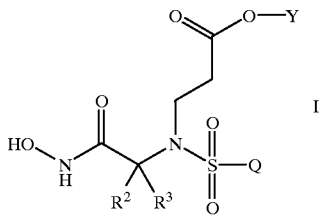

I

Scheme 1 refers to the preparation of matrix metalloproteinase inhibiting compounds of formula I.

Referring to Scheme 1, compounds of said formula I are prepared from compounds of formula II by reaction with an in situ formed silyated hydroxylamine followed by treatment with an acid. Specifically, in situ formed silyated hydroxylamine compounds are prepared by reaction of hydroxylamine hydrochloride or hydroxylamine sulfate, preferably hydroxylamine hydrochloride, with a $((C_1-C_4)\text{alkyl})_3$silyl halide in the presence of a base to form O-trimethylsilylhydroxylamine, N,O-bistrimethylsilylhydroxylamine or combinations thereof. Suitable bases include pyridine, 2,6-lutidine or diisopropylethylamine, preferably pyridine. The reaction is performed at a temperature of about 0° to about 22° C. (i.e., room temperature) for about 1 to about 12 hours, preferably about 1 hour. Suitable acids include hydrochloric or sulfuric, preferably hydrochloric.

Compounds of said formula II, preferably not isolated, are prepared from compounds of formula III, wherein $R^4$ is hydrogen, by reaction with oxalyl chloride or thionyl chloride, preferably oxalyl chloride, and a catalyst, preferably about 2% of N,N-dimethylformamide, in an inert solvent such as methylene chloride or toluene. The reaction is performed at a temperature of about 0° to about 22° C. (i.e., room temperature) for about 1 to about 12 hours, preferably about 1 hour.

Compounds of the formula III, wherein $R^4$ is hydrogen, can be prepared from compounds of the formula IV, wherein $R^1$ is optionally substituted benzyl, by reduction in a polar solvent. Suitable reducing agents include palladium catalysts with a source of hydrogen, such as hydrogen over palladium, hydrogen over palladium on carbon or palladium hydroxide on carbon, preferably hydrogen over palladium on carbon. Suitable solvents include tetrahydrofuran, methanol, ethanol and isopropanol and mixtures thereof, preferably ethanol. The aforesaid reaction is performed at a temperature of about 22° C. (i.e., room temperature) for a period of 1 to 7 days, preferably about 2 days.

Compounds of the formula III, wherein $R^5$ is other than hydrogen, such as a protonated amine (such as protonated primary amine, secondary amine or tertiary amine), alkali metal or alkaline earth metal, can be prepared from compounds of the formula III, wherein $R^5$ is hydrogen, by treatment with an aqueous or alkanolic solution containing an acceptable cation (e.g., sodium, potassium, dicyclohexylamine, calcium and magnesium, preferably dicyclohexylamine), and then evaporating the resulting solution to dryness, preferably under reduced pressure or filtering the precipitate, preferably the dicyclohexylamine salt precipate.

Compounds of the formula IV, wherein $R^1$ is $(C_1-C_6)$ alkyl or optionally substituted benzyl, can be prepared from compounds of the formula V, wherein $R^1$ is optionally substituted benzyl, by Michael addition to a propiolate ester in the presence of a base in a polar solvent. Suitable propiolates are of the formula H—C≡C—CO$_2$Y, wherein Y is $(C_1-C_6)$alkyl. Compounds of the formula H—C≡C—CO$_2$Y are commercially available or can be made by methods well known to those of ordinary skill in the art. Suitable bases include tetrabutylammonium fluoride, potassium carbonate, tertiary amines and cesium carbonate, preferably tetrabutylammonium fluoride. Suitable solvents include tetrahydrofuran, acetonitrile, tert-butanol, t-amyl alcohols and N,N-dimethylformamide, preferably tetrahydrofuran. The aforesaid reaction is performed at a temperature of about −10° C. to about 60° C., preferably ranging between 0° C. and about 22° C. (i.e., room temperature). The compounds of formula IV are obtained as mixtures of geometric isomers about the olefinic double bond (i.e. cis and trans isomers); separation of the isomers is not necessary.

Compounds of said formula I, wherein Y is $(C_1-C_6)$alkyl, can be saponified to the free acid (i.e. Y is hydrogen) using a base such as sodium hydroxide in a protic solvent such as ethanol, methanol or water or a mixture such as water and ethanol, water and toluene, or water and THF. The preferred solvent system is water and toluene. The reaction is conducted for a period of 30 minutes to 24 hours, preferably about 2 hours.

Compounds of the formula V, wherein $R^1$ is optionally substituted benzyl can be prepared according to methods known in the art. The alkylsulfonamides that can be prepared by the methods of the present invention and the starting materials of formula V are also described in the literature. PCT Publications WO 96/27583 and WO 98/07697, published Mar. 7, 1996 and Feb. 26, 1998, respectively, refer to arylsulfonyl hydroxamic acids. Each of the above referenced publications is hereby incorporated by reference in its entirety.

Compounds of the formula V wherein $R^2$ and $R^3$ are tetrahydropyran-4-yl or a bicyclo ring of the formula

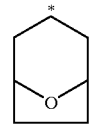

wherein the asterisk indicates the carbon atom common to $R^2$ and $R^3$ can be prepared according to methods analogous to those of Examples 2 and 3.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The ability of the compounds of formula I or their pharmaceutically acceptable salts (hereinafter also referred to as the active compounds) to inhibit matrix metalloproteinases or ADAMs (such as inhibiting the production of tumor necrosis factor (TNF)) and, consequently, demonstrate their effectiveness for treating diseases characterized by matrix metalloproteinase or ADAM (such as the production of tumor necrosis factor) can be determined according to in vitro assay tests well known to those of ordinary skill in the art. One example of an assay recognized as demonstrating that the final products produced by the methods of the invention is the following Inhibition of Human Collagenase Assay.

ADDITIONAL PREFERRED EXAMPLES OF THE INVENTION

The present invention is also directed to enhanced methodology for the preparation of compounds such as structure (formula) I in Scheme I (see the Detailed Description of the Invention below),

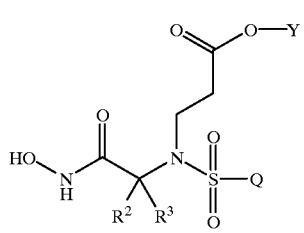

I and to novel process intermediates useful in this regard. The compounds of structure I have valuable pharmacological activities. Accordingly, there are provided preferred intermediate compounds according to structure IV as aforementioned,

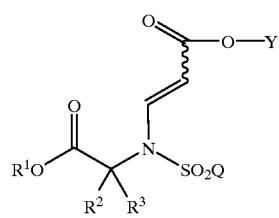

IV in which $R^1$ is $[(A_1)CH_2]_c[(A_2)CH_2]_b[(A_3)CH_2]_aC-$, where a, b, and c are each 1; and each of $A_1$, $A_2$, and $A_3$ is independently selected from the group consisting of H, $(C_1-C_5)$ alkyl, and phenyl or substituted phenyl. In a preferred example $R^1$ is t-butyl; and thus $A_1$, $A_2$, $A_3$ are each hydrogen.

The provision of such intermediate compounds facilitates high yield synthesis of pharmaceutical compounds of the invention. It has been determined that in the Michael addition reaction (see below, for its use in preliminary synthetic steps herein) wherein a compound of the formula

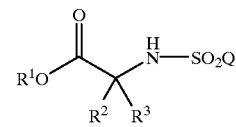

is reacted with a compound of the formula

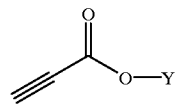

substantial and surprising advantage results if the $R^1$ group is defined according to this particular example of the invention (that is, $R^1$ is $[(A_1)CH_2]_c[(A_2)CH_2]_b[(A_3)CH_2]_aC-$, where a, b, and c are each 1; and each of $A_1$, $A_2$, and $A_3$ is independently selected from the group consisting of H, $(C_1-C_5)$ alkyl, and phenyl or substituted phenyl). This is seen in comparison with other examples of $R^1$ as defined by the present disclosure, including for example the benzyl or optionally substituted benzyl group. Accordingly use of, for example, t-butyl as $R^1$ is preferred over nonetheless highly useful groups such as, for example, benzyl.

The benzyl and substituted benzyl groups are very useful as $R^1$ according to the practice of the present invention. For example, with respect to the structure

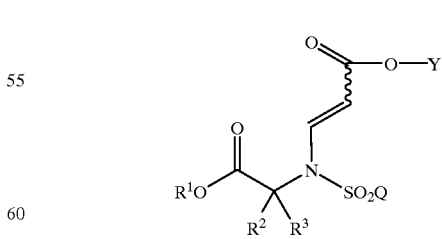

IV reaction conditions can be chosen (see above) such that in one step, not only is the carbon—carbon double bond reduced, but benzyl is cleaved from the carboxyl group. Although this would seem very advantageous, it appears that the presence of benzyl or substituted benzyl at $R^1$ permits side reactions that may detract from the overall efficiency of the intended Michael addition. Although the practice of the invention is not limited by any theory, it appears that enhancing the efficiency of the Michael reaction, even at the expense of simplicity of later steps, may be of significant importance in determining the efficiency of the overall synthetic scheme. Thus, the present example provides an alternative to other useful technology of the invention.

Again, without being limited as to theory, it may be that $R^1$ groups such as t-butyl interfere with side reactions (such as through steric hindrance) more so than other $R^1$ groups, such as benzyl, during the Michael addition. This effect may be more important to the overall reaction success that direct coupling efficiency. Accordingly, the practice of the present invention includes an alternate effective means to generate the intermediate compounds needed for efficient production herein of active pharmaceuticals.

The present invention therefore provides processes for preparing compounds such as

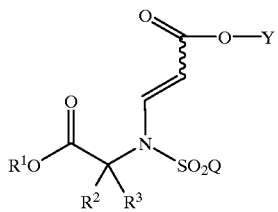

IV in which $R^1$ is $[(A_1)CH_2]_c[(A_2)CH_2]_b[(A_3)CH_2]_aC—$, where a, b, and c are each 1; and each of $A_1$, $A_2$, and $A_3$ is independently selected from the group consisting of H, $(C_1-C_5)$ alkyl, and phenyl or substituted phenyl, and processes for the further use thereof.

With respect to the selection of $R^1$ groups herein, it is expected that additional groups having the effect of t-butyl, may be utilized or others discovered, based upon the general teachings herein. Accordingly, the skilled practitioner will realize that it is within the practice of the present invention to utilize generally as $R^1$ any group that, relative to benzyl, detracts from the rate of side reactions during the Michael addition.

Such further processes include reducing said compound IV

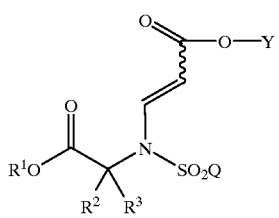

IV wherein $R^1$ is $[(A_1)CH_2]_c[(A_2)CH_2]_b[(A_3)CH_2]_aC—$, where a, b, and c are each 1; and each of $A_1$, $A_2$, and $A_3$ is independently selected from the group consisting of H, $(C_1-C_5)$ alkyl, and phenyl or substituted phenyl, and $R^2$, $R^3$, Y and Q are as defined above, with a reducing agent to form a compound of the formula

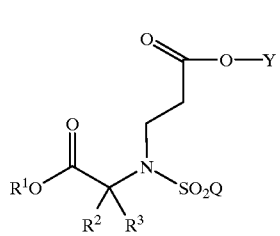

(i)

In a further aspect of the invention, said methodology further comprises hydrolyzing the above compound, wherein $R^1$, $R^2$, $R^3$, Y and Q are as defined in above, under acidic conditions to form a compound of the formula

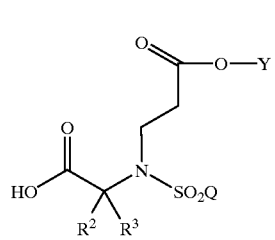

(ii)

wherein $R^2$, $R^3$, Y and Q are as defined above.

In connection with the selection of Y groups for the practice of the present invention, it is noted that Y is preferably selected as hydrogen or $(C_1-C_6)$alkyl in the compounds of the invention. With respect to the aforementioned processes (consider the conversion of structure (i) to structure (ii) directly above), it is highly preferred that Y be $(C_1-C_6)$alkyl. The $(C_1-C_6)$alkyl group possesses a particularly valuable property in that although it is labile to hydrolysis under alkaline conditions, it is suitably resistant to hydrolysis under acidic conditions useful in the practice of the invention. Thus, when $R^1$ is t-butyl, for example, a preferential hydrolysis may be performed under moderately acidic conditions (see, for example, Example 4) cleaving the t-butyl group while leaving the Y moiety in place as a functional group. Since the Y $(C_1-C_6)$alkyl group, in comparison with the newly exposed carboxyl group, is resistant to both acid chloride formation and the subsequent hydroxamic acid introduction, the final chemistry of the invention may be directed to the appropriate carbonyl group as intended. It is within the practice of the present invention to utilize other moities, besides the $(C_1-C_6)$alkyl group to achieve this same functional result.

In an additional embodiment of the invention, a compound of the formula

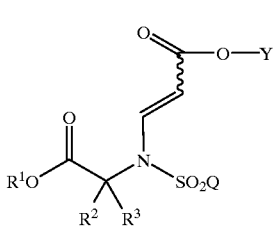

IV wherein $R^1$, $R^2$, $R^3$, Y and Q are as defined above, is first subject to hydrolysis under acidic conditions to form a compound of the formula

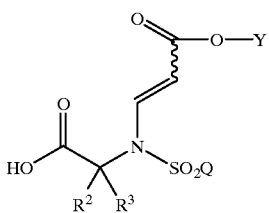

(a)

wherein $R^2$, $R^3$, Y and Q remain as defined above; and then subject to a second step in which compound (a) is treated with a reducing agent to form a compound of the formula

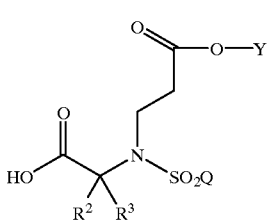

(b)

wherein $R^2$, $R^3$, Y and Q are defined as above.

In connection with the aforementioned reactions, it may be mentioned that hydrolysis under acidic conditions may involve use of various acids. Among the mineral acids, HCl, HBr, and $H_2SO_4$ may be mentioned. Appropriate carboxylic acids such as formic and trifluoroacetic acid may also be used. Without limitation, an additional class of useful acids includes sulfonic acids such as p-toluene sulfonic acid and methanesulfonic acid.

With respect to reducing conditions mentioned as useful according to the practice of this aspect of the invention, the following is noted. Suitable catalytic conditions result when the reducing agent is hydrogen over a catalyst that is selected from the group consisting of platinum oxide or Raney nickel, or a supported catalyst that is selected from the group consisting of palladium on carbon, or platinum on carbon. Again, it will be recognized that it is within the skill of the art to identify equivalently effective agents and conditions.

Biological Assay
Inhibition of Human Collagenase (MMP-1)

Human recombinant collagenase is activated with trypsin using the following ratio: 10 μg trypsin per 100 μg of collagenase. The trypsin and collagenase are incubated at room temperature for 10 minutes then a five fold excess (50 μg/10 μg trypsin) of soybean trypsin inhibitor is added.

10 mM stock solutions of inhibitors are made up in dimethyl sulfoxide and then diluted using the following Scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 μl is then added to appropriate wells of the microfluor plate. Final concentration of collagenase in the assay is 100 ng/ml.

Substrate (DNP-Pro-Cha-Gly-Cys(Me)-His-Ala-Lys (NMA)-$NH_2$) is made as a 5 mM stock in dimethyl sulfoxide and then diluted to 20 mM in assay buffer. The assay is initiated by the addition of 50 μl substrate per well of the microfluor plate to give a final concentration of 10 μM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). $IC_{50}$'s are determined from the concentration of inhibitor that gives a signal that is 50% of the control.

If $IC_{50}$'s are reported to be <0.03 μM then the inhibitors are assayed at concentrations of 0.3 μM, 0.03 μM, 0.03 μM and 0.003 μM.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

3-[[4-(4-FLUOROPHENOXY) BENZENESULFONYL]-(1-HYDROXYCARBAMOYL-CYCLOPENTYL) AMINO]PROPIONIC ACID

A) 1-[4-(4-Fluorophenoxy)benzenesulfonylamino] cyclopentanecarboxylic Acid Benzyl Ester To a mixture of 12.41 g (0.032 mol) of 1-aminocyclopentanecarboxylic acid benzyl ester, toluene-4-sulfonic acid salt (can be prepared according to literature methods such as those described in U.S. Pat. No. 4,745,124), and 10.0 g (0.035 mol, 1.1 equivalents) of 4-(4-fluorophenoxy)benzenesulfonyl chloride (prepared according to Preparation 3) in 113 mL of toluene was added 11.0 mL (0.079 mol, 2.5 equivalents) of triethylamine. The resulting mixture was stirred at ambient temperature overnight, washed with 2N hydrochloric acid (2×100 mL) and brine (100 mL), dried over sodium sulfate, and concentrated to 30 mL. Hexane, 149 mL, was added drop-wise over three hours giving a solid precipitate which was granulated at 0° C. for one hour and filtered yielding 12.59 g (85%) of 1-[4-(4-fluorophenoxy)benzenesulfonylamino] cyclopentane-carboxylic acid benzyl ester.

$^1$H NMR ($CDCl_3$) δ 7.78–7.82 (m, 2H), 7.30–7.39 (m, 5H), 7.06–7.12 (m, 2H), 6.99–7.04 (m, 2H), 6.93–6.97 (m, 2H), 5.15 (s, 1H), 5.02 (s, 2H), 2.04–2.13 (m, 2H), 1.92–1.98 (m, 2H), 1.62–1.69 (m, 4H).

A 4.0 g sample was granulated in a mixture of 4 mL of ethyl acetate and 40 mL of hexanes overnight giving 3.72 g (93% recovery) of 1-[4-(4-fluorophenoxy)benzenesulfonyl-amino]-cyclopentanecarboxylic acid benzyl ester as light tan solids, mp 97.0–97.5° C.

B) 1-{(2-Ethoxycarbonylvinyl)-[4-(4-fluorophenoxy)benzenesulfonyl]-amino}cyclopentanecarboxylic Acid Benzyl Ester A solution of 25.0 g (53.2 mmol) of 1-[4-(4-fluorophenoxy)benzenesulfonylamino]-cyclopentanecarboxylic acid benzyl ester and 10.8 mL (106 mmol, 2 equivalents) of ethyl propiolate in 200 mL of dry tetrahydrofuran at 1° C. was treated with 53.2 mL (53.2 mmol, 1 equivalent) of a solution of tetrabutylammonium fluoride in tetrahydrofuran (1M) over 45 minutes. The resulting solution was allowed to warm slowly to ambient temperature and stirred overnight. The tetrahydrofuran was displaced with toluene at reduced pressure, and the toluene solution was washed with water and brine, diluted to 600 mL with toluene, stirred with 90 g of silica gel for three hours, filtered, and concentrated to 25.14 g (83%) of 1-{(2-ethoxycarbonylvinyl)-[4-(4-fluorophenoxy)benzenesulfonyl]amino}-cyclopentanecarboxylic acid benzyl ester as an orange oil. $^1$H NMR (CDCl$_3$) indicated a 1.5:1 trans/cis ratio.

Trans δ 7.74–7.78 (m, 2H), 7.72 (d, J=14 Hz, 1H), 7.26–7.36 (m, 5H), 6.96–7.12 (m, 4H), 6.78–6.84 (m, 2H), 5.44 (d, J=14 Hz, 1H), 5.11 (s, 2H), 4.12 (q, J=7.1 Hz, 2H), 2.08–2.43 (m, 4H), 1.63–1.80 (m, 4H), 1.24 (t, J=7.1 Hz, 3H). Cis δ 7.68–7.72 (m, 2H), 7.26–7.36 (m, 5H), 6.96–7.12 (m, 4H), 6.86–6.91 (m, 2H), 6.47 (d, J=8.1 Hz, 1H), 5.90 (d, J=8.1 Hz, 1H), 5.11 (s, 2H), 3.93 (q, J=7.2 Hz, 2H), 2.08–2.43 (m, 4H), 1.63–1.80 (m, 4H), 1.17 (t, J=7.2 Hz, 3H).

C) 1-{(2-Ethoxycarbonylethyl)-[4-(4-fluorophenoxy)benzenesulfonyl]-amino}-cyclopentanecarboxylic Acid A solution of 2.50 g (4.4 mmol) of 1-{(2-ethoxycarbonylvinyl)-[4-(4-fluorophenoxy)benzenesulfonyl]amino}cyclopentanecarboxylic acid benzyl ester in 25 mL of ethanol was treated with 2.5 g of 50% water wet 10% palladium on carbon catalyst and shaken under 53 psi of hydrogen for 21 hours. The catalyst was removed by filtration and washed with ethanol (4×25 mL). The filtrate and washings were combined and concentrated under vacuum to 1.74 g (82%) of crude 1-{(2-ethoxycarbonylethyl)-[4-(4-fluorophenoxy)benzenesulfonyl]amino}cyclopentanecarboxylic acid as a viscous oil.

$^1$H NMR (CDCl$_3$) δ 7.78–7.82 (m, 2H), 6.94–7.09 (m, 6H), 4.09 (q, J=7.2 Hz, 2H), 3.56–3.60 (m, 2H), 2.75–2.79 (m, 2H), 2.33–2.39 (m, 2H), 1.93–2.03 (m, 2H), 1.69–1.76 (m, 2H), 1.56–1.63 (m, 2H), 1.22 (t, J=7.2 Hz, 3H).

D) 1-{(2-Ethoxycarbonylethyl)-[4-(4-fluorophenoxy)benzenesulfonyl]-amino}-cyclopentanecarboxylic Acid, Dicyclo hexylaminium Salt A solution of 3.10 g (6.5 mmol) of crude 1-{(2-ethoxycarbonylethyl)-[4-(4-fluorophenoxy)benzenesulfonyl]amino}cyclopentanecarboxylic acid in 30 mL of ethanol was treated with 1.28 mL (6.5 mmol, 1 equivalent) of dicyclohexylamine at ambient temperature producing solids within five minutes. This mixture was stirred at ambient temperature overnight and then at 0° C. for five hours. White solids were isolated by filtration, washed with 10 mL of cold ethanol, and air dried giving 2.89 g (67%) of 1-{(2-ethoxycarbonylethyl)-[4-(4-fluorophenoxy)benzene sulfonyl]amino}cyclopentanecarboxylic acid, dicyclohexylaminium salt.

$^1$H NMR (CDCl$_3$) δ 7.86–7.91 (m, 2H), 6.99–7.09 (m, 4H), 6.90–6.94 (m, 2H), 5.3 (br s, 2H), 4.07 (q, J=7.1 Hz, 2H), 3.54–3.59 (m, 2H), 2.88–2.95 (m, 4H), 2.31–2.38 (m, 2H), 1.95–2.22 (m, 6H), 1.68–1.77 (m, 6H), 1.53–1.60 (m, 4H), 1.40–1.50 (m, 4H), 1.21 (t, J=7.1 Hz, 3H), 1.14–1.22 (m, 6H). Mp 164.5–165.9° C.

E) 1-{(2-Ethoxycarbonylethyl)-[4-(4-fluorophenoxy)benzenesulfonyl]-amino}-cyclopentanecarboxylic Acid A solution of 3.0 g (4.5 mmol) of 1-{(2-ethoxycarbonylethyl)-[4-(4-fluorophenoxy)benzenesulfonyl]amino}cyclopentanecarboxylic acid, dicyclohexylaminium salt in 30 mL of dichloromethane was treated with 30 mL of 2N hydrochloric acid at ambient temperature causing immediate precipitation of solids. This mixture was stirred at ambient temperature for three hours. The solids were filtered, the aqueous phase was extracted with dichloromethane, and the combined organic phases were washed with water, dried over sodium sulfate, and concentrated under vacuum to 2.2 g (100%) of 1-{(2-ethoxycarbonylethyl)-[4-(4-fluorophenoxy)benzenesulfonyl]amino}cyclopentanecarboxylic acid as a clear oil.

$^1$H NMR (DMSO-d$_6$) δ 12.68 (bs, 1H), 7.76–7.80 (m, 2H), 7.25–7.31 (m, 2H), 7.16–7.21 (m, 2H), 7.03–7.08 (m, 2H), 4.01 (q, J=7.1 Hz, 2H), 3.48–3.54 (m, 2H), 2.64–2.70 (m, 2H), 2.13–2.21 (m, 2H), 1.90–1.98 (m, 2H), 1.52–1.59 (m, 4H), 1.14 (t, J=7.1 Hz, 3H).

F) 3-{(1-Chlorocarbonylcyclopentyl)-[4-(4-fluorophenoxy)benzene-sulfonyl]amino}propionic Acid Ethyl Ester A solution of 7.26 g (15.1 mmol) of 1-{(2-ethoxycarbonylethyl)-[4-(4-fluorophenoxy)benzenesulfonyl]amino}cyclopentanecarboxylic acid in 73 mL of dichloromethane was treated with 1.4 mL (17 mmol, 1.1 equivalents) of oxalyl chloride and 0.02 mL (0.3 mmol, 0.02 equivalents) of dimethylformamide at ambient temperature, causing some bubbling, and was is stirred overnight. The resulting solution of 3-{(1-chlorocarbonylcyclopentyl)-[4-(4-fluorophenoxy)benzenesulfonyl]amino}propionic acid ethyl ester was used for the preparation of 3-[[4-(4-fluorophenoxy)benzenesulfonyl]-(1-hydroxycarbamoylcyclopentyl)amino] propionic acid ethyl ester without isolation.

A similarly prepared solution of 3-{(1-chlorocarbonylcyclopentyl)-[4-(4-fluorophenoxy)benzenesulfonyl]amino}propionic acid ethyl ester was concentrated under vacuum to an oil.

$^1$H NMR (CDCl$_3$) δ 7.84–7.87 (m, 2H), 6.97–7.12 (m, 6H), 4.10 (q, J=7.2 Hz, 2H), 3.55–3.59 (m, 2H), 2.68–2.72 (m, 2H), 2.47–2.53 (m, 2H), 1.95–2.02 (m, 2H), 1.71–1.76 (m, 4H), 1.24 (t, J=7.2 Hz, 3H).

G) 3-[[4-(4-Fluorophenoxy)benzenesulfonyl]-(1-hydroxycarbamoylcyclo-pentyl)amino]propionic Acid Ethyl Ester A solution of 1.37 g (19.7 mmol, 1.3 equivalents) of hydroxylamine hydrochloride in 9.2 mL (114 mmol, 7.5 equivalents) of dry pyridine at 0° C. was treated with 5.8 mL (45 mmol, 3.0 equivalents) of trimethylsilyl chloride, causing white solids to precipitate. The mixture was allowed to warm to ambient temperature overnight. This mixture was then cooled to 0° C. and treated with a solution of 7.54 g (15.1 mmol) of 3-{(1-chlorocarbonylcyclopentyl)-[4-(4-fluorophenoxy)benzenesulfonyl]amino}propionic acid ethyl ester in 73 mL of dichloromethane, prepared as described above, without isolation, causing an exotherm to about 8° C. This mixture was stirred at 0° C. for 30 minutes and at ambient temperature for about one hour. The reaction was then treated with 50 mL of 2N aqueous hydrochloric acid and was stirred at ambient temperature for one hour. The aqueous phase was extracted with dichloromethane and the combined organic phases were washed with 2N aqueous hydrochloric acid (2×50 mL) and water (50 mL). This solution of 3-[[4-(4-fluorophenoxy)benzenesulfonyl]-(1-hydroxycarbamoylcyclopentyl)amino]propionic acid ethyl ester in dichloromethane was used for the preparation of 3-[[4-(4-fluorophenoxy)benzenesulfonyl]-(1-hydroxycarbamoylcyclopentyl)amino]propionic acid without isolation. An aliquot was concentrated to a foam.

$^1$H NMR (DMSO-d$_6$) δ 10.37 (s, 1H), 8.76 (s, 1H), 7.74–7.79 (m, 2H), 7.24–7.30 (m, 2H), 7.14–7.20 (m, 2H), 7.01–7.05 (m, 2H), 3.99 (q, J=7.1 Hz, 2H), 3.42–3.47 (m, 2H), 2.62–2.67 (m, 2H), 2.16–2.23 (m, 2H), 1.77–1.85 (m, 2H), 1.43–1.52 (m, 4H), 1.13 (t, J=7.1 Hz, 3H).

A similarly prepared solution was concentrated under vacuum to 6.71 g (89%) of 3-[[4-(4-fluorophenoxy)benzenesulfonyl]-(1-hydroxy carbamoylcyclopentyl)amino] propionic acid ethyl ester as a hard dry foam.

H) 3-[[4-(4-Fluorophenoxy)benzenesulfonyl]-(1-hydroxycarbamoylcyclo-pentyl)amino]propionic Acid A solution of 7.48 g (15.1 mmol) of 3-[[4-(4-fluorophenoxy)benzenesulfonyl]-(1-hydroxycarbamoylcyclopentyl)amino]propionic acid ethyl ester in dichloromethane was concentrated by rotary evaporation with the addition of 75 mL of toluene. This solution was treated with 75 mL of water, cooled to 0° C., and treated with 6.05 g (151 mmol, 10 equivalents) of sodium hydroxide pellets over 10 minutes with vigorous stirring. This mixture was stirred for 15 minutes at 0° C. and warmed to ambient temperature over one hour. The aqueous phase was separated, diluted with 7.5 mL of tetrahydrofuran, cooled to 0° C., and treated with 33 mL of 6N aqueous hydrochloric acid over 20 minutes. This mixture was stirred with 75 mL of ethyl acetate at 0° C. to ambient temperature, and the ethyl acetate phase was separated and washed with water. The ethyl acetate solution was slowly treated with 150 mL of hexanes at ambient temperature causing solids to precipitate, and was stirred overnight. Filtration yielded 5.01 g of 3-[[4-(4-fluorophenoxy)benzenesulfonyl]-(1-hydroxy carbamoylcyclopentyl) amino]propionic acid as a white solid (71% yield from 1-{(2-ethoxycarbonylethyl)-[4-(4-fluorophenoxy) benzenesulfonyl] amino}cyclopentanecarboxylic acid).

$^1$H NMR (DMSO-d$_6$) δ 12.32 (s, 1H), 10.43 (s, 1H), 8.80 (s, 1H), 7.82 (d, J=8.6 Hz, 2H), 7.28–7.35 (m, 2H), 7.20–7.26 (m, 2H), 7.08 (d, J=8.9 Hz, 2H), 3.44–3.49 (m, 2H), 2.61–2.66 (m, 2H), 2.24–2.29 (m, 2H), 1.86–1.90 (m, 2H), 1.54–1.55 (m, 4H). mp 162.9–163.5° C. (dec).

EXAMPLE 2

3-[[4-(4-Fluoro-phenoxy)-benzenesulfonyl]-(4-hydroxycarbamoyl-tetrahydro-pyran-4-yl)-amino]-propionic acid A) 4-[N-(Diphenylmethylene)amino]tetrahydropyran-4-carboxylic acid benzyl ester To a suspension of sodium hydride (6.56 grams. 0.164 mole) in ethylene glycol dimethyl ether (150 mL) at 0° C. is added a solution of the N-(diphenylmethylene)glycine benzyl ester (0.07398 mole) in ethylene glycol dimethyl ether (50 mL) dropwise via addition funnel. A solution of 2-bromoethyl ether (23.21 grams, 0.090 mole) in ethylene glycol dimethyl ether (50 mL) is then added, in 10 mL portions over approximately 5 minutes, to the ethylene glycol dimethyl ether solution. The ice bath is removed and the reaction is stirred at room temperature for 16 hours. The mixture is diluted with diethyl ether and washed with water. The aqueous layer is extracted with diethyl ether. The combined organic extracts are washed with brine, dried over magnesium sulfate, and concentrated to afford crude product. Chromatography on silica gel eluting first with 4 L of 5% ethyl acetate/hexane followed by 4 liters of 10% ethyl acetate/hexane provides 4-[N-(diphenylmethylene)amino] tetrahydropyran-4-carboxylic acid benzyl ester as a clear yellow oil.

B) 4-Aminotetrahydropyran-4-carboxylic acid benzyl ester

To a solution of 4-[N-(diphenylmethylene)amino] tetrahydropyran-4-carboxylic acid benzyl ester (0.047 mole) in diethyl ether (120 mL) is added 1M aqueous hydrochloric acid solution (100 mL). The mixture is stirred vigorously at room temperature for 16 hours. The layers are separated and the aqueous layer washed with diethyl ether. The aqueous layer is brought to pH 10 with dilute aqueous ammonium hydroxide solution and extracted with dichloromethane. The organic extract is dried over sodium sulfate and concentrated to give 4-aminotetrahydropyran-4-carboxylic acid benzyl ester.

C) 4-[4-(4-Fluorophenoxy)benzenesulfonylamino] tetrahydropyran-4-carboxylic acid benzyl ester To a solution of 4-aminotetrahydropyran-4-carboxylic acid benzyl ester (0.0404 mole) in N,N-dimethylformamide (40 mL) is added triethylamine (5.94 mL, 0.043 mole). Solid 4-(4-fluorophenoxy)benzenesulfonyl chloride (12.165 grams, 0.0424 mole) is added to the above solution in portions. The resulting mixture is stirred at room temperature for 16 hours and then most of the solvent is removed by evaporation under vacuum. The residue was partitioned between saturated sodium bicarbonate solution and dichloromethane. The aqueous layer is separated and extracted with dichloromethane. The combined organic layers are washed with brine and dried over sodium sulfate. Evaporation of the solvent under vacuum provided crude 4-[4-(4-fluorophenoxy)benzenesulfonylamino]tetrahydropyran-4-carboxylic acid benzyl ester. Flash chromatography on silica gel eluting with 25% ethyl acetate/hexane followed by 50% ethyl acetate/hexane provided 4-[4-(4-fluorophenoxy) benzenesulfonylamino]tetrahydropyran-4-carboxylic acid benzyl ester.

D) 4-{(2-Ethoxycarbonyl-vinyl)-[4-(4-fluoro-phenoxy) benzenesulfonyl]-amino}-tetrahydro-pyran-4-carboxylic acid benzyl ester A solution of (53.2 mmol) of the product of the previous step and 10.8 mL (106 mmol, 2 equivalents) of ethyl propiolate in 200 mL of dry tetrahydrofuran at 1° C. is treated with 53.2 mL (53.2 mmol, 1 equivalent) of a solution of tetrabutylammonium fluoride in tetrahydrofuran (1M) over 45 minutes. The resulting solution is allowed to warm slowly to ambient temperature and stirred overnight. The tetrahydrofuran is displaced with toluene at reduced pressure, and the toluene solution is washed with water and brine, diluted to 600 mL with toluene, stirred with 90 g of silica gel for three hours, filtered, and concentrated to the title compound.

E) 4-{(2-Ethoxycarbonyl-ethyl)-[4-(4-fluoro-phenoxy) benzenesulfonyl]-amino}-tetrahydro-pyran-4-carboxylic acid A solution of (4.4 mmol) of the product of step D in 25 mL of ethanol is treated with 2.5 g of 50% water wet 10% palladium on carbon catalyst and shaken under 53 psi of hydrogen for 21 hours. The catalyst is removed by filtration and washed with ethanol (4×25 mL). The filtrate and washings are combined and concentrated under vacuum to crude product.

F) 3-{(4-Chlorocarbonyl-tetrahydro-pyran-4-yl)-[4-(4-fluorophenoxy)-benzenesulfonyl]-amino}-propionic acid ethyl ester A solution of (15.1 mmol) of the product from Step E in 73 mL of dichloromethane is treated with 1.4 mL (17 mmol, 1.1 equivalents) of oxalyl chloride and 0.02 mL (0.3 mmol, 0.02 equivalents) of dimethylformamide at ambient temperature, causing some bubbling, and is stirred overnight. The resulting solution of the title compound is used in step G without isolation.

G) 3-[[4-(4-Fluoro-phenoxy)-benzenesulfonyl]-(4-hydroxycarbamoyl-tetrahydro-pyran-4-yl)-amino]-propionic acid ethyl ester A solution of (19.7 mmol, 1.3 equivalents) of hydroxylamine hydrochloride in 9.2 mL (114 mmol, 7.5 equivalents) of dry pyridine at 0° C. is treated with 5.8 mL (45 mmol, 3.0 equivalents) of trimethylsilyl chloride, causing white solids to precipitate. The mixture is allowed to warm to ambient temperature overnight. This mixture is then cooled to 0° C. and treated with a solution of (15.1 mmol) of the product from Step F in 73 mL of dichloromethane causing an exotherm to about 8° C. This mixture is stirred at 0° C. for 30 minutes and at ambient temperature for about one hour. The reaction is then treated with 50 mL of 2N aqueous hydrochloric acid and was stirred at ambient temperature for one hour. The aqueous phase is extracted with dichloromethane and the combined organic phases are washed with 2N aqueous hydrochloric acid (2×50 mL) and water (50 mL). This solution of the title compound in dichloromethane is used in the next step.

(H) 3-[[4-(4-Fluoro-phenoxy)-benzenesulfonyl]-(4-hydroxycarbamoyl-tetrahydro-pyran-4-yl)-amino]-propionic acid A solution of 15.1 mmoles of the product from Step G in dichloromethane is concentrated by rotary evaporation with the addition of 75 mL of toluene. This solution is treated with 75 mL of water, cooled to 0° C., and treated with 6.05 g (151 mmol, 10 equivalents) of sodium hydroxide pellets over 10 minutes with vigorous stirring. This mixture is stirred for 15 minutes at 0° C. and warmed to ambient temperature over one hour. The aqueous phase is separated, diluted with 7.5 mL of tetrahydrofuran, cooled to 0° C., and treated with 33 mL of 6N aqueous hydrochloric acid over 20 minutes. This mixture is stirred with 75 mL of ethyl acetate at 0° C. to ambient temperature, and the ethyl acetate phase is separated and washed with water. The ethyl acetate solution was concentrated to yield the title compound.

EXAMPLE 3

3-[[4-(4-Fluoro-phenoxy)-benzenesulfonyl]-(3-hydroxycarbamoyl-8-oxa-bicyclo[3.2.1]oct-3-yl)-amino]-propionic acid A) 3-(Benzhydrylideneamino)-8-oxabicyclo[3.2.1]octane-3-carboxylic acid benzyl ester To a suspension of sodium hydride (0.41 grams, 17.1 mmole) in N,N-dimethylformamide (50 mL) at 0° C. is added dropwise a solution of N-diphenylmethylene glycine benzyl ester (7.8 mmole) in N,N-dimethylformamide (50 mL). After stirring for 30 minutes at room temperature, a solution of cis-2,5-bis(hydroxymethyl)-tetrahydrofuran ditosylate (4.1 grams, 9.3 mmole) (prepared by literature methods such as those described in JOC, 47, 2429–2435 (1982)) in N,N-dimethylformamide (50 mL) is added dropwise. The reaction mixture is gradually heated to 100° C. in an oil bath and stirred at this temperature overnight. The solvent is evaporated under vacuum and the residue is taken up in water and extracted twice with diethyl ether. The combined organic extracts are washed with brine, dried over magnesium sulfate and concentrated to a crude product.

B) 3-Amino-8-oxabicyclo[3.2.1]octane-3-carboxylic acid benzyl ester hydrochloride A two-phase mixture of 3-(benzhydrylideneamino)-8-oxabicyclo[3.2.1]octane-3-carboxylic acid benzyl ester (3.9 mmole) in aqueous 1N hydrochloric acid solution (100 mL) and diethyl ether (100 mL) is stirred at room temperature overnight. The aqueous layer is concentrated to provide the title compound.

C) 3-exo-[4-(4-Fluorophenoxy)benzenesulfonylamino]-8-oxabicyclo[3.2.1]-octane-3-carboxylic acid benzyl ester A solution of 3-amino-8-oxabicyclo[3.2.1]octane-3-carboxylic acid benzyl ester hydrochloride (2.9 mmole), 4-(4-fluorophenoxy)benzenesulfonylchloride (923 mg, 3.2 mmole) and triethylamine (0.9 mL, 6.5 mmole) in N,N-dimethylformamide (45 mL) is stirred at room temperature overnight. The solvent is removed under vacuum and the residue is taken up in saturated aqueous sodium bicarbonate solution. After extracting twice with methylene chloride, the combined organic layers are washed with brine, dried over magnesium sulfate and concentrated to a brown oil. The title compound is isolated by chromatography on silica using 1% methanol in methylene chloride as eluant.

D) 3-{(2-Ethoxycarbonyl-vinyl)-[4-(4-fluoro-phenoxy)-benzenesulfonyl]-amino}-8-oxa-bicyclo[3.2.1]octane-3-carboxylic acid benzyl ester A solution of (53.2 mmol) of the product of the previous step and 10.8 mL (106 mmol, 2 equivalents) of ethyl propiolate in 200 mL of dry tetrahydrofuran at 1° C. is treated with 53.2 mL (53.2 mmol, 1 equivalent) of a solution of tetrabutylammonium fluoride in tetrahydrofuran (1M) over 45 minutes. The resulting solution is allowed to warm slowly to ambient temperature and stirred overnight. The tetrahydrofuran is displaced with toluene at reduced pressure, and the toluene solution is washed with water and brine, diluted to 600 mL with toluene, stirred with 90 g of silica gel for three hours, filtered, and concentrated to the title compound.

E) 3-{(2-Ethoxycarbonyl-ethyl)-[4-(4-fluoro-phenoxy)-benzenesulfonyl]-amino}-8-oxa-bicyclo[3.2.1]octane-3-carboxylic acid A solution of (4.4 mmol) of the product of step D in 25 mL of ethanol is treated with 2.5 g of 50% water wet 10% palladium on carbon catalyst and shaken under 53 psi of hydrogen for 48 hours. The catalyst is removed by filtration and washed with ethanol (4×25 mL). The filtrate and washings are combined and concentrated under vacuum to crude product.

F) 3-{(3-Chlorocarbonyl-8-oxa-bicyclo[3.2.1]oct-3-yl)-[4-(4-fluoro-phenoxy)-benzene sulfonyl]-amino}-propionic acid ethyl ester A solution of 15.1 mmoles of the product from Step E in 73 mL of dichloromethane is treated with 1.4 mL (17 mmol, 1.1 equivalents) of oxalyl chloride and 0.02 mL (0.3 mmol, 0.02 equivalents) of dimethylformamide at ambient temperature, causing some bubbling, and is stirred overnight. The resulting solution of the title compound is used in step G without isolation.

G) 3-[[4-(4-Fluoro-phenoxy)-benzenesulfonyl]-(3-hydroxycarbamoyl-8-oxa-bicyclo[3.2.1]oct-3-yl)-amino]-propionic acid ethyl ester A solution of (19.7 mmol, 1.3 equivalents) of hydroxylamine hydrochloride in 9.2 mL (114 mmol, 7.5 equivalents) of dry pyridine at 0° C. is treated with 5.8 mL (45 mmol, 3.0 equivalents) of trimethylsilyl chloride, causing white solids to precipitate. The mixture is allowed to warm to ambient temperature overnight. This mixture is then cooled to 0° C. and treated with a solution of (15.1 mmol) of the product from Step F in 73 mL of dichloromethane causing an exotherm to about 8° C. This mixture is stirred at 0° C. for 30 minutes and at ambient temperature for about one hour. The reaction is then treated with 50 mL of 2N aqueous hydrochloric acid and was stirred at ambient temperature for one hour. The aqueous phase is extracted with dichloromethane and the combined organic phases are washed with 2N aqueous hydrochloric acid (2×50 mL) and water (50 mL). This solution of the title compound in dichloromethane is used in the next step.

(H) 3-[[4-(4-Fluoro-phenoxy)-benzenesulfonyl]-(3-hydroxycarbamoyl-8-oxa-bicyclo[3.2.1]oct-3-yl)-amino]-propionic acid A solution of 15.1 mmoles of the product from Step G in dichloromethane is concentrated by rotary evaporation with the addition of 75 mL of toluene. This solution is treated with 75 mL of water, cooled to 0° C., and treated with 6.05 g (151 mmol, 10 equivalents) of sodium hydroxide pellets over 10 minutes with vigorous stirring. This mixture is stirred for 15 minutes at 0° C. and warmed to ambient temperature over one hour. The aqueous phase is separated, diluted with 7.5 mL of tetrahydrofuran, cooled to 0° C., and treated with 33 mL of 6N aqueous hydrochloric acid over 20 minutes. This mixture is stirred with 75 mL of ethyl acetate at 0° C. to ambient temperature, and the ethyl acetate phase is separated and washed with water. The ethyl acetate solution was concentrated to yield the title compound.

PREPARATION 1
4-(4-Fluorophenoxy)benzenesulfonic Acid 4-Fluorophenyl Ester

A solution of 14.68 g (0.131 mol, 2.0 equivalents) of potassium tert-butoxide in 27 mL of dry N-methylpyrrolidinone was treated with a solution of 15.39 g (0.137 mol, 2.1 equivalents) of 4-fluorophenol in 27 mL of dry N-methylpyrrolidinone at ambient temperature causing a mild exotherm to 45° C. A solution of 13.81 g (0.065 mol) of 4-chlorobenzenesulfonyl chloride in 27 mL of dry N-methylpyrrolidinone was slowly added to the dark reaction mixture causing a mild exotherm to 44° C. The resulting mixture was stirred at room temperature for one hour and then at 130° C. for 11 hours. The cooled reaction mixture was treated with 162 mL of water, seeded with a trace of 4-(4-fluorophenoxy)benzenesulfonic acid 4-fluorophenyl ester, and granulated at room temperature overnight. The resulting solids were filtered yielding 20.24 g (85%) of 4-(4-fluorophenoxy)benzenesulfonic acid 4-fluorophenyl ester.

$^1$H NMR (CDCl$_3$) δ 7.74 (dd, J=7.0, 2.0 Hz, 2H), 7.14–6.97 (m, 10H). mp 78–83° C.

PREPARATION 2
4-(4-Fluorophenoxy)benzenesulfonic Acid, Sodium Salt

To a slurry of 47.43 g (0.131 mol) of 4-(4-fluorophenoxy)benzenesulfonic acid 4-fluorophenyl ester in 475 mL of ethanol was added 13.09 g (0.327 mol, 2.5 equivalents) of sodium hydroxide pellets. This mixture was heated at reflux for three hours and stirred overnight at room temperature. The resulting solids were filtered yielding 37.16 g (98%) of 4-(4-fluorophenoxy)benzenesulfonic acid, sodium salt.

$^1$H NMR (CD$_3$OD) δ 7.73–7.78 (m, 2H), 7.05–7.13 (m, 2H), 6.99–7.05 (m, 2H), 6.90–6.95 (m, 2H).

PREPARATION 3
4-(4-Fluorophenoxy)benzenesulfonyl Chloride

To a slurry of 15.0 g (0.052 mol) of 4-(4-fluorophenoxy)benzenesulfonic acid☐, sodium salt, in 150 mL of dry toluene was added 11.3 mL (0.155 mol, 3 equivalents) of thionyl chloride and 0.04 mL (0.5 mmol, 0.01 equivalents) of dimethylformamide. The resulting mixture was stirred at room temperature for 48 hours, filtered through diatomaceous earth, and concentrated under reduced pressure to 40 mL. This solution was used without further purification to prepare 1-[4-(4-fluorophenoxy)benzenesulfonylamino] cyclopentanecarboxylic acid benzyl ester.

A 5.0 mL portion of this solution was concentrated to 1.77 g of 4-(4-fluorophenoxy)benzenesulfonyl chloride as an oil, corresponding to a 96% yield.

$^1$H NMR (CDCl$_3$) δ 7.92–7.97 (m, 2H), 7.01–7.13 (m, 6H). A portion of similarly prepared oil was crystallized from hexane, mp 80° C.

EXAMPLE 4
PREPARATION 1
1-[4-(4-Fluoro-phenoxy)-benzenesulfonylamino]-cyclopentanecarboxylic acid 1-[4-(4-Fluoro-phenoxy)-benzenesulfonylamino]-cyclopentanecarboxylic acid benzyl ester (15 g, 32 mmole) in 75 mL THF was combined with 75 mL (150 mmole) 2N aqueous sodium hydroxide and stirred at reflux for 1 hour. The reaction was cooled to ambient temperature and diluted with 100 mL water and 100 mL ethyl acetate. The pH of the aqueous phase was adjusted to pH 1.2 and the ethyl acetate layer separated. The ethyl acetate layer was washed with 100 mL water and dried over magnesium sulfate. The ethyl acetate was stripped in vacuo and replaced with 75 mL methyl tert-butyl ether. The product was filtered and dried to yield 11.16 g (92%) of 1-[4-(4-fluoro-phenoxy)benzenesulfonylamino]-cyclopentanecarboxylic acid. $^1$H NMR (CDCl$_3$) ☐ 7.71–7.78 (m, 2H), 6.88–7.04 (m, 6H), 5.04 (s, 1H), 2.01–2.13 (m, 2H), 1.92–1.98 (m, 2H), 1.44–1.68 (m, 4H).

PREPARATION 2
1-[4-(4-Fluoro-phenoxy)-benzenesulfonylamino]-cyclopentanecarboxylic acid tert-butyl ester To a solution of 1-[4-(4-fluoro-phenoxy) benzenesulfonylamino]-cyclopentanecarboxylic acid (10.22 g, 27 mmole) in 100 mL methylene chloride at –78☐ C. was condensed 40 mL of isobutylene. Concentrated sulfuric acid (0.3 mL) was added and the mixture allowed to warm to ambient temperature and stirred for 22 hours. The mixture was then washed with 3×50 mL 2N NaOH and the organic layer dried over magnesium sulfate and evaporated to give 11.17 g (95%) of 1-[4-(4-fluoro-phenoxy)-benzenesulfonylamino]-cyclopentanecarboxylic acid tert-butyl ester. $^1$H NMR (CDCl$_3$) ☐ 7.74–7.77 (m, 2H), 6.85–7.13 (m, 6H), 4.95 (s, 1H), 1.92–2.02 (m, 2H), 1.78–1.88 (m, 2H), 1.50–1.65 (m, 4H), 1.35 (s, 9H).

The practitioner of the art will recognize numerous other strategies for synthesis of the reaction intermediates described herein. For example, esterification with isobutylene can be accomplished on a molecule such as

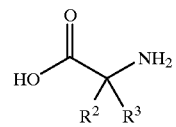

followed by sulfanation with, for example, a QSO$_2$Cl moiety. Alternatively, it is noted that, for example, t-butyl esters of the above structures are readily prepared, or may be commercially available.

PREPARATION 3
1-{(2-Ethoxycarbonyl-vinyl)-[4-(4-fluoro-phenoxy)-benzenesulfonyl]-amino}-cyclopentanecarboxylic acid tert-butyl ester To a mixture of 1-[4-(4-fluoro-phenoxy)-benzenesulfonylamino]-cyclopentanecarboxylic acid tert-butyl ester (1.0 g, 2.3 mmole) in 10 mL THF and 2.3 mL (2.3 mmole) 1M tetrabutylammonium fluoride in THF was added 0.23 mL (2.3 mmole) ethyl propiolate at ambient temperature. After stirring 1 hour the reaction was complete by HPLC and was stripped to dryness in vacuo. The residue was dissolved in 20 mL ethyl acetate and washed with 2×10 mL water and the organic solution stripped to an oil. This oil was chromatographed over silica gel, eluting with 10% ethyl acetate/hexane to yield 0.95 g (77% yield) 1-{(2-ethoxycarbonyl-vinyl)-[4-(4-fluoro-phenoxy)-benzenesulfonyl]-amino}-cyclopentanecarboxylic acid tert-butyl ester as a colorless oil. $^1$H NMR (CDCl$_3$) indicated a 1.5:1 trans/cis ratio.

Trans □ 7.79–7.83 (m, 2H), 7.63 (d, J=14 Hz, 1H), 6.89–7.05 (m, 4H), 5.44 (d, J=14 Hz, 1H), 4.08 (q, J=7.1 Hz, 1H), 2.08–2.43 (m, 4H), 1.63–1.80 (m, 4H), 1.39 (s, 9H), 1.22 (t, J=7.1 Hz, 3H). Cis 7.62–7.69 (m, 2H), 6.91–6.85 (m, 2H), 6.55 (d, J=8.1 Hz, 1H), 5.85 (d, J=8.1 Hz, 1H), 3.81 (q, J=7.2 Hz, 2H), 2.08–2.43, m, 4H), 1.19–1.25, m, 4H), 1.49 (s, 9H), 1.11 (q, J=7.2 Hz, 3H).

PREPARATION 4

1-{(2-Ethoxycarbonyl-ethyl)-[4-(4-fluoro-phenoxy)-benzenesulfonyl]-amino}-cyclopentanecarboxylic acid tert-butyl ester A solution of 1-{(2-Ethoxycarbonyl-vinyl)-[4-(4-fluoro-phenoxy)-benzenesulfonyl]-amino}-cyclopentanecarboxylic acid tert-butyl ester (1.23 g, 2.3 mmole) in 50 mL ethanol with 723 mg 5% Pd/C catalyst was hydrogenated at ambient temperature until HPLC indicated that the reaction was complete. The catalyst was filtered and the filtrate evaporated to give an oil which was submitted to chromatography over silica gel, eluting with 105 ethyl acetate in hexane. 1-{(2-Ethoxycarbonyl-ethyl)-[4-(4-fluoro-phenoxy)-benzenesulfonyl]-amino}-cyclopentanecarboxylic acid tert-butyl ester was isolated as a colorless oil (875 mg, 71% yield). $^1$H NMR (CDCl$_3$) □ 7.75–7.80 (m, 2H), 6.86–7.01 (m, 6H), 4.09 (q, J=7.2, 2H), 3.44–3.48 (m, 2H), 2.66–2.72, m, 2H), 2.09–2.15 (m, 2H), 1.52–1.74, m, 4H), 1.43 (s, 9H), 1.21 (t, J=7.2 Hz, 3H).

PREPARATION 5

1-{(2-Ethoxycarbonyl-ethyl)-[4-(4-fluoro-phenoxy)-benzenesulfonyl]-amino}-cyclopentanecarboxylic acid, Dicyclo hexylaminium salt A solution of 1-{(2-ethoxycarbonyl-ethyl)-[4-(4-fluoro-phenoxy)-benzenesulfonyl]-amino}-cyclopentanecarboxylic acid tert-butyl ester (0.225 g, 0.42 mmole) in 4 mL toluene was treated with methane sulfonic acid (0.06 mL, 0.84 mmole) and 18 hours at ambient temperature. The solution was washed with aqueous sodium bicarbonate solution and evaporated to a colorless oil. The oil was dissolved in 2 mL ethanol and treated with dicyclohexyl amine (0.084 mL, 0.42 mmole). The product, 1-{(2-ethoxycarbonyl-ethyl)-[4-(4-fluoro-phenoxy)-benzenesulfonyl]-amino}-cyclopentanecarboxylic acid, dicyclohexylaminium salt, was filtered and dried to give 223 mg (80% yield) of a white solid which had an identical HPLC retention time and NMR to a sample prepared from the benzyl ester route.

What is claimed is:
1. A compound of the formula

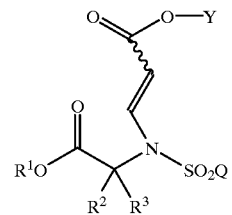

wherein $R^1$ is $[(A_1)CH_2]_c[(A_2)CH_2]_b[(A_3)CH_2]_aC-$, where a, b, and c are each 1; and each of $A_1$, $A_2$, and $A_3$ is independently selected from the group consisting of H, $(C_1-C_5)$ alkyl, and phenyl or substituted phenyl; $R^2$ and $R^3$ are independently $(C_1-C_6)$alkyl or $R^2$ and $R^3$ are taken together to form a three to seven membered cycloalkyl, pyran-4-yl ring or a bicyclo ring of the formula

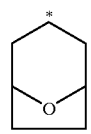

wherein the asterisk indicates the carbon atom common to $R^2$ and $R^3$;

Q is $(C_1-C_6)$alkyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_6-C_{10})$aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_6-C_{10})$aryl$(C_6-C_{10})$aryl, $(C_6-C_{10})$aryl$(C_6-C_{10})$aryl$(C_2-C_9)$heteroaryl, $(C_6-C_{10})$aryl$(C_2-C_9)$heteroaryl, $(C_2-C_9)$heteroaryl, $(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryloxy$(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$alkoxy$(C_1-C_6)$alkyl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl;

wherein each $(C_6-C_{10})$aryl or $(C_2-C_9)$heteroaryl moieties of said $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_6-C_{10})$aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_6-C_{10})$aryl$(C_6-C_{10})$aryl, $(C_6-C_{10})$aryl$(C_2-C_9)$heteroaryl, $(C_2-C_9)$heteroaryl, $(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryloxy$(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$alkoxy$(C_1-C_6)$alkyl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro$(C_1-C_3)$alkyl, perfluoro$(C_1-C_3)$alkoxy and $(C_6-C_{10})$aryloxy;

and Y is hydrogen, or $(C_1-C_6)$alkyl.

2. The compound of claim 1 wherein $R^2$ and $R^3$ are taken together to form a cyclobutyl, cyclopentyl, pyran-4-yl ring or a bicyclo ring of the formula

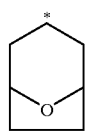

wherein the asterisk indicates the carbon atom common to $R^2$ and $R^3$.

3. The compound of claim 1 wherein Q is 4-(4-fluorophenoxy)phenyl.

4. A process for preparing a compound of the formula

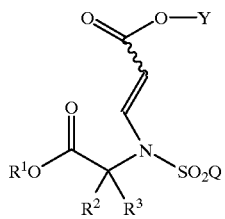

wherein $R^1$ is $[(A_1)CH_2]_c[(A_2)CH_2]_b[(A_3)CH_2]_aC-$, where a, b, and c are each 1; and each of $A_1$, $A_2$, and $A_3$ is independently selected from the group consisting of H, $(C_1-C_5)$ alkyl, and phenyl or substituted phenyl;

$R^2$ and $R^3$ are independently $(C_1-C_6)$alkyl or $R^2$ and $R^3$ are taken together to form a three to seven membered cycloalkyl, a pyran-4-yl ring or a bicyclo ring of the formula

wherein the asterisk indicates the carbon atom common to $R^2$ and $R^3$;

Q is $(C_1-C_6)$alkyl, $(C_6-C_{10})$aryl, $(C_2-C_9)$heteroaryl, $(C_6-C_{10})$aryloxy$(C_1-C_6)$alkyl, $(C_6-C_{10})$aryloxy $(C_6-C_{10})$aryl, $(C_6-C_{10})$aryloxy$(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_6-C_{10})$aryl$(C_6-C_{10})$aryl, $(C_6-C_{10})$aryl$(C_6-C_{10})$aryl$(C_2-C_9)$heteroaryl, $(C_2-C_9)$heteroaryl$(C_1-C_6)$alkyl, $(C_2-C_9)$heteroaryl$(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10}$aryl$(C_1-C_6)$alkoxy$(C_2-C_9)$heteroaryloxy $(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$alkoxy$(C_1-C_6)$alkyl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl;

wherein each $(C_6-C_{10})$aryl or $(C_2-C_9)$heteroaryl moieties of said $(C_6-C_{10})$aryl, $(C_2-C_9)$heteroaryl, $(C_6-C_{10})$aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_6-C_{10})$aryl$(C_6-C_{10})$aryl, $(C_6-C_{10})$aryl$(C_6-C_{10})$aryl$(C_2-C_9)$heteroaryl, $(C_2-C_9)$heteroaryl$(C_1-C_6)$alkyl, $(C_2-C_9)$heteroaryl$(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl$(C_1-C_6)$alkoxy $(C_2-C_9)$heteroaryl, $(C_2-C_9)$heteroaryloxy$(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$alkoxy$(C_1-C_6)$alkyl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro $(C_1-C_3)$alkyl, perfluoro$(C_1-C_3)$alkoxy and $(C_6-C_{10})$ aryloxy;

and Y is $(C_1-C_6)$alkyl;

comprising, reacting a compound of the formula

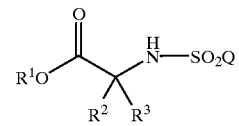

wherein $R^1$, $R^2$, $R^3$ and Q are as defined above;

with a compound of the formula

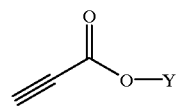

wherein Y is $(C_1-C_6)$alkyl;

in the presence of a base and a polar solvent.

5. The process according to claim 4, wherein said base is tetrabutylammonium fluoride.

6. The process according to claim 4, wherein said solvent is tetrahydrofuran.

7. The process according to claim 4, further comprising the step of reducing said compound of the formula

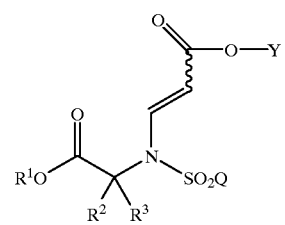

wherein $R^1$, $R^2$, $R^3$ Y and Q are as defined in claim 4;

with a reducing agent to form a compound of the formula

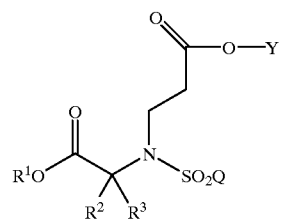

wherein R¹, R², R³, Y and Q are as defined above.

8. The process according to claim 7, wherein said reducing agent is hydrogen over a catalyst that is selected from the group consisting of platinum oxide or Raney nickel, or a supported catalyst that is selected from the group consisting of palladium on carbon, or platinum on carbon.

9. The process according to claim 7, wherein said reduction is conducted in ethanol as solvent.

10. The process according to claim 7, further comprising hydrolyzing said compound of the formula,

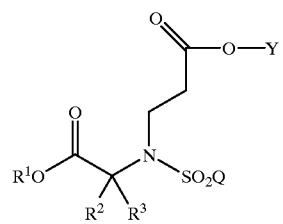

wherein R¹, R², R³, Y and Q are as defined in claim 7, under acidic conditions to form a compound of the formula

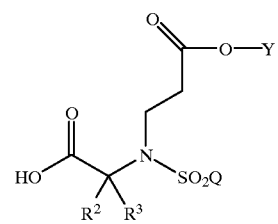

wherein R², R³, Y and Q are as defined above.

11. The process according to claim 4, comprising:
(a) a first further step of hydrolyzing said compound of the formula

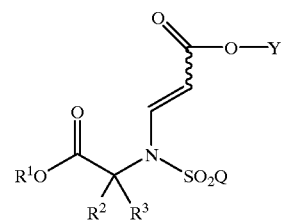

wherein R¹, R², R³, Y and Q are as defined in claim 4, under acidic conditions to form a compound of the formula (a)

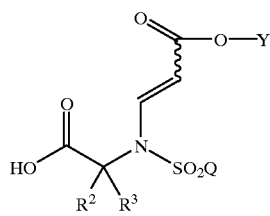

wherein R², R³, Y and Q are as defined above; and (b) a second further step of reducing said compound (a) with a reducing agent to form a compound of the formula (b)

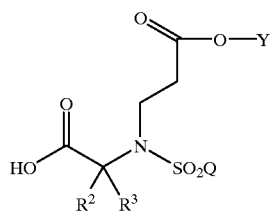

wherein R², R³, Y and Q are defined as above.

12. The process according to claim 11, wherein said reducing agent is hydrogen over a catalyst that is selected from the group consisting of platinum oxide or Raney nickel, or a supported catalyst that is selected from the group consisting of palladium on carbon, or platinum on carbon.

* * * * *